US008268334B2

(12) United States Patent
Dreilinger et al.

(10) Patent No.: US 8,268,334 B2
(45) Date of Patent: Sep. 18, 2012

(54) AQUEOUS ACIDIC HARD SURFACE CLEANING AND DISINFECTING COMPOSITIONS

(75) Inventors: Lisa Dreilinger, Montvale, NJ (US); Matthew James Kaser, Montvale, NJ (US)

(73) Assignee: Reckitt Benckiser LLC, Parsippany, NJ (US)

( * ) Notice: Subject to any disclaimer, the term of this patent is extended or adjusted under 35 U.S.C. 154(b) by 0 days.

(21) Appl. No.: 12/740,830

(22) PCT Filed: Oct. 20, 2008

(86) PCT No.: PCT/GB2008/003542

§ 371 (c)(1), (2), (4) Date: Jun. 4, 2010

(87) PCT Pub. No.: WO2009/060171

PCT Pub. Date: May 14, 2009

(65) Prior Publication Data

US 2010/0240752 A1 Sep. 23, 2010

Related U.S. Application Data

(60) Provisional application No. 60/986,095, filed on Nov. 7, 2007, provisional application No. 61/090,374, filed on Aug. 20, 2008.

(51) Int. Cl.
*A61K 9/00* (2006.01)

(52) U.S. Cl. .................................................... 424/400

(58) Field of Classification Search .................. 424/400
See application file for complete search history.

(56) References Cited

U.S. PATENT DOCUMENTS

| | | | | |
|---|---|---|---|---|
| 3,697,573 | A * | 10/1972 | Danzik et al. | 558/37 |
| 4,861,511 | A * | 8/1989 | Kaplan | 510/193 |
| 5,707,952 | A * | 1/1998 | Lambremont et al. | 510/362 |
| 5,707,957 | A | 1/1998 | Yianakopoulos et al. | |
| 6,221,823 | B1 * | 4/2001 | Crisanti et al. | 510/238 |
| 6,492,313 | B1 | 12/2002 | Connors et al. | |
| 6,617,296 | B1 | 9/2003 | Connors et al. | |
| 6,864,222 | B1 * | 3/2005 | Manske | 510/463 |

FOREIGN PATENT DOCUMENTS

| | | | |
|---|---|---|---|
| GB | 2306500 | A | 5/1997 |
| GB | 2392167 | * | 2/2004 |
| GB | 2392167 | A | 2/2004 |
| GB | 2429016 | A | 2/2007 |
| WO | 2004074421 | A | 9/2004 |
| WO | 2006131690 | A | 12/2006 |

OTHER PUBLICATIONS

Ryan and Kaler. Colloids and Surfaces A: Physicochemical and Engineering Aspects 176 (2001) 69-83.*
BASF. Lutensol ON MSDS, Jan. 23, 2007.*
BASF2 (Lutensol ON types, Apr. 2005).*

* cited by examiner

*Primary Examiner* — David J Blanchard
*Assistant Examiner* — Devang Thakor
(74) *Attorney, Agent, or Firm* — Norris McLaughlin & Marcus PA

(57) ABSTRACT

A highly aqueous liquid acidic hard surface treatment composition having a pH of about 3.5 or less which necessarily comprises:

0.001-3.5% wt. of an acid constituent which comprises one or more organic acids, but which preferably comprises lactic acid and one or more further organic acids acids, and especially preferably wherein the acid constituent consists solely of lactic acid;

an organic solvent constituent, desirably selected from a monohydric alcohol and/or a glycol ether;

an anionic surfactant constituent, desirably a sulfur atom containing anionic surfactant constituent, such as of the sulfate or sulfonate types;

a nonionic surfactant constituent;

optionally a cosurfactant constituent, including one or more nonionic, cationic, amphoteric or zwitterionic surfactants;

optionally one or more further constituents selected coloring agents, fragrances and fragrance solubilizers, viscosity modifying agents including one or more thickeners, pH adjusting agents and pH buffers including organic and inorganic salts, optical brighteners, opacifying agents, hydrotropes, abrasives, and preservatives, as well as other optional constituents known to the art;

and the balance, water, wherein water comprises at least 80% wt. of the composition.

The highly aqueous liquid acidic hard surface treatment composition may be used as such, or may be used to impregnate absorbent substrates to form wipe articles.

Methods for the use of said highly aqueous liquid acidic hard surface treatment compositions, in cleaning and/or disinfection of hard surfaces are also disclosed.

8 Claims, No Drawings

AQUEOUS ACIDIC HARD SURFACE CLEANING AND DISINFECTING COMPOSITIONS

This is an application filed under 35 USC 371 of PCT/GB2008/003542

The present invention relates to aqueous acidic hard surface cleaning compositions.

Hard surface cleaning compositions are commercially important products and enjoy a wide field of use, and are known in assisting in the removal of dirt and grime from surfaces, especially those characterized as useful for cleaning "hard surfaces". Certain of such hard surface cleaning compositions also exhibit efficacy in providing a disinfecting or sanitizing benefit as well. While the prior art provides a variety of compositions which provide effective cleaning of various types of stains, there is nonetheless a continuing need in the art to provide improved hard surface cleaning compositions which provide a sanitizing or disinfecting benefit and which are also effective in the treatment of many types of stains typically encountered on hard surfaces, particularly in a home or commercial environment, especially in or around kitchens where cleanliness is of particular importance. It is to such needs that the compositions of the present invention are particularly directed.

Broadly, the present invention relates to liquid acidic hard surface treatment compositions which are effective against common stains encountered on hard surfaces, particularly greasy soils or stains, and which also provide a germicidal/disinfecting benefit to treated surfaces.

In one specific aspect there is provided a highly aqueous liquid acidic hard surface treatment composition having a pH of about 3.5 or less which necessarily comprises:

0.001-3.5% wt. of an acid constituent which comprises one or more organic acids, but which preferably comprises lactic acid and one or more further organic acids acids, and especially preferably wherein the acid constituent consists solely of lactic acid;

an organic solvent constituent, desirably selected from a monohydric alcohol and/or a glycol ether;

an anionic surfactant constituent, desirably a sulfur atom containing anionic surfactant constituent, such as of the sulfate or sulfonate types;

a nonionic surfactant constituent;

optionally a cosurfactant constituent, including one or more nonionic, cationic, amphoteric or zwitterionic surfactants;

optionally one or more further constituents selected coloring agents, fragrances and fragrance solubilizers, viscosity modifying agents including one or more thickeners, pH adjusting agents and pH buffers including organic and inorganic salts, optical brighteners, opacifying agents, hydrotropes, abrasives, and preservatives, as well as other optional constituents known to the art;

and the balance, water, wherein water comprises at least 80% wt. of the composition.

In certain preferred embodiments the anionic surfactant constituent is based on one or more sulfate or sulfonate anionic surfactants, preferably to the exclusion of one or more anionic surfactants of types other than the sulfate or sulfonate anionic surfactants.

In yet further preferred embodiments the compositions expressly include in the organic solvent constituent one or more $C_1$-$C_6$ monohydric alcohols and/or glycol ethers, preferably to the exclusion of other organic solvent constituents.

In certain preferred embodiments there are provided as vendible articles, dispensing containers comprising the hard surface treatment compositions described herein.

In further preferred embodiments there are provided carrier substrates, e.g., wipes, sponges, and the like comprising the hard surface treatment compositions as described herein.

The present invention also provides for methods for the treatment of stained hard surfaces in need of cleaning which comprises the step of applying a cleaning effective amount of the acidic hard surface treatment composition as described herein to a hard surface in need of a cleaning treatment.

The present invention also provides for methods for the treatment of stained hard surfaces in need of disinfection or sanitizing which comprises the step of applying a disinfection or sanitizing effective amount of the acidic hard surface treatment composition as described herein to a hard surface in need of a disinfection or sanitizing treatment.

The present invention also provides for compositions which exhibit good cleaning properties against dirt and stains commonly found in household, commercial and residential settings, particularly in kitchen settings wherein greasy soils and stains are frequently encountered.

These and further aspects of the invention including especially preferred aspects thereof, will become more apparent from the present specification.

The compositions of the invention necessarily comprise an acid constituent comprising one or more organic acids. Exemplary organic acids are those which generally include at least one carbon atom, and include at least one carboxyl group (—COOH) in its structure. Exemplary useful water soluble organic acids which contain from 1 to about 6 carbon atoms, and at least one carboxyl group as noted. Exemplary useful organic acids include: linear aliphatic acids such as acetic acid, citric acid, propionic acid, butyric acid and valeric acid; dicarboxylic acids such as malonic acid, succinic acid, glutaric acid, adipic acid, pimelic acid, fumaric acid and maleic acid; acidic amino acids such as glutamic acid and aspartic acid; and hydroxy acids such as glycolic acid, lactic acid, hydroxyacrylic acid, α-hydroxybutyric acid, glyceric acid, tartronic acid, malic acid, tartaric acid and citric acid, as well as acid salts of these organic acids. The use of water soluble acids are preferred, including water soluble salts of organic acids. The acid constituent of the present invention forms 0.001-3.5% wt. of the hard surface treatment compositions of which they form a part and especially desirably the acid constituent comprises lactic acid and one or more further organic acids, but especially preferably wherein the acid constituent consists solely of lactic acid to the exclusion of other co-acids, including inorganic acids as well as other organic acids, or alternately wherein the acid constituent consists solely of a binary or ternary mixture of lactic acid with one or both of citric acid and/or malic acid, e.g. lactic acid and citric acid, or lactic acid and malic acid or lactic acid, citric acid and malic acid.

The inventive compositions may optionally include one or more co-acids based on one or more inorganic acids. Exemplary inorganic acids for use as co-acids in the present invention include phosphoric acid, potassium dihydrogenphosphate, sodium dihydrogenphosphate, sodium sulfite, potassium sulfite, sodium pyrosulfite (sodium metabisulfite), potassium pyrosulfite (potassium metabisulfite), acid sodium hexametaphosphate, acid potassium hexametaphosphate, acid sodium pyrophosphate, acid potassium pyrophosphate and sulfamic acid. Alkyl sulfonic acids, e.g., methane sulfonic acid may also be used as a co-acid component of the acid system. Strong inorganic acids such as hydrochloric acid, nitric acid and sulfuric acid may also be used, however are less preferred due to their strong acidic character; if present are present in only minor amounts. However, the use of water soluble acids as co-acids are preferred, including water soluble salts of organic acids. When present, the co-acids based on one or more inorganic acids may be included in any effective amount in order to provide or contribute to providing a desired pH to the hard surface treatment compositions taught herein. Advantageously they are present in amounts of from 0-5% wt., preferably from 0.001-4% wt. based on the total weight of the treatment composition of which they form a part. In certain preferred embodiments one or more co-acids based on one or more inorganic acids are necessarily present, while in other preferred embodiments one or more co-acids based on one or more inorganic acids are expressly excluded as noted above.

As the inventive compositions are necessarily acidic in nature and exhibit a pH of not more than 3.5. Preferably the pH of the inventive compositions is between 0.001-3.5, more preferably is between 0.1-3.25, yet more preferably is between 1 and 3.25, and especially preferably is between 2 and 3.2. Certain particularly preferable pHs are demonstrated with reference to one or more of the Examples described hereinafter.

The compositions of the invention necessarily include an organic solvent constituent.

Exemplary useful organic solvents are those which are at least partially water-miscible such as alcohols, water-miscible ethers (e.g. diethylene glycol diethylether, diethylene glycol dimethylether, propylent glycol dimethylether), water-miscible glycol ether (e.g. propylene glycol monomethylether, propylene glycol mono ethylether, propylene glycol monopropylether, propylene glycol monobutylether, ethylene glycol monobutylether, dipropylene glycol monomethylether, diethyleneglycol monobutylether), lower esters of monoalkylethers of ethyleneglycol or propylene glycol (e.g. propylene glycol monomethyl ether acetate) all commercially available from Union Carbide, Dow Chemicals or Hoescht. Glycol ethers having the general structure Ra—Rb—OH, wherein Ra is an alkoxy of 1 to 20 carbon atoms, or aryloxy of at least 6 carbon atoms, and Rb is an ether condensate of propylene glycol and/or ethylene glycol having from one to ten glycol monomer units are advantageously used.

Further exemplary useful organic solvents include phenyl containing glycol ether solvents including those which may be represented by the following general structural representation (I):

(I)

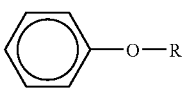

wherein R is a $C_1$-$C_6$ alkyl group which contains at least one —OH moiety, and preferably R is selected from: $CH_2OH$, $CH_2CH_2OH$, $CH(OH)CH_3$, $CH(OH)CH_2OH$, $CH_2CH_2CH_2OH$, $CH_2CH(OH)CH_3$, $CH(OH)CH_2CH_3$, $CH(OH)CH_2CH_2OH$, $CH(OH)CH(OH)CH_3$, and $CH(OH)CH(OH)CH_2OH$, and the phenyl ring may optionally substituted with one or more further moieties such as $C_1$-$C_3$ alkyl groups but is preferably unsubstituted. A specific useful phenyl containing glycol ether solvent is commercially supplied as DOWANOL PPH, described to be a propylene glycol phenyl ether which is described by it supplier as being represented by the following structural representation (II):

(II)

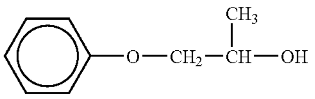

and further, indicated is that the major isomer is as indicated, which suggests that other alkyl isomers are also present.

Mixtures of two or more specific organic solvents may be used, or alternately a single organic solvent may be provided as the organic solvent constituent.

Preferably the organic solvent constituent consists solely of one or more of $C_1$-$C_6$ monohydric alcohols and/or glycol ethers to the exclusion of other organic solvents. In certain preferred embodiments the organic solvent constituent consists solely of one or more of $C_1$-$C_6$ monohydric alcohols to the exclusion of other organic solvents, e.g., glycol ethers, while in other preferred embodiments the organic solvent constituent consists solely of one or more glycol ethers to the exclusion of other organic solvents, e.g., glycol ethers.

The organic solvent constituent may be present in effective amounts. Advantageously the organic solvent constituent is present in amount of from 0.01% wt. to about 10% wt, preferably are present in amounts of from about 0.01-5% wt., and yet more preferably in amounts of from about 0.05-3% wt.

The hard surface treatment compositions of the invention necessarily include an anionic surfactant constituent. Exemplary of anionic surfactants which may be present in the anionic surfactant constituent include alcohol sulfates and sulfonates, alcohol phosphates and phosphonates, alkyl ester sulfates, alkyl diphenyl ether sulfonates, alkyl sulfates, alkyl ether sulfates, sulfate esters of an alkylphenoxy polyoxyethylene ethanol, alkyl monoglyceride sulfates, alkyl sulfonates, alkyl ether sulfates, alpha-olefin sulfonates, beta-alkoxy alkane sulfonates, alkyl ether sulfonates, ethoxylated alkyl sulfonates, alkylaryl sulfonates, alkylaryl sulfates, alkyl monoglyceride sulfonates, alkyl carboxylates, alkyl ether carboxylates, alkyl alkoxy carboxylates having 1 to 5 moles of ethylene oxide, alkylpolyglycolethersulfates (containing up to 10 moles of ethylene oxide), sulfosuccinates, octoxynol or nonoxynol phosphates, taurates, fatty taurides, fatty acid amide polyoxyethylene sulfates, acyl glycerol sulfonates, fatty oleyl glycerol sulfates, alkyl phenol ethylene oxide ether sulfates, paraffin sulfonates, alkyl phosphates, isethionates, N-acyl taurates, alkyl succinamates and sulfosuccinates, alkylpolysaccharide sulfates, alkylpolyglucoside sulfates, alkyl polyethoxy carboxylates, and sarcosinates or mixtures thereof. These anionic surfactants may be provided as salts with one or more organic counterions, e.g, ammonium, or inorganic counteraions, especially as salts of one or more alkaline earth or alkaline earth metals, e.g, sodium.

Further examples of anionic surfactants include water soluble salts or acids of the formula $(ROSO_3)_xM$ or $(RSO_3)_xM$ wherein R is preferably a $C_6$-$C_{24}$ hydrocarbyl, preferably an alkyl or hydroxyalkyl having a $C_{10}$-$C_{20}$ alkyl component, more preferably a $C_{12}$-$C_{18}$ alkyl or hydroxyalkyl, and M is H or a mono-, di- or tri-valent cation, e.g., an alkali metal cation (e.g., sodium, potassium, lithium), or ammonium or substituted ammonium (e.g., methyl-, dimethyl-, and trimethyl ammonium cations and quaternary ammonium cations, such as tetramethyl-ammonium and dimethyl piperidinium cations and quaternary ammonium cations derived from alkylamines such as ethylamine, diethylamine, triethylamine, and mixtures thereof, and the like) and x is an integer, preferably 1 to 3, most preferably 1. Materials sold under the Hostapur and Biosoft trademarks are examples of such anionic surfactants.

Still further examples of anionic surfactants include alkyldiphenyl-ethersulphonates and alkyl-carboxylates.

Other anionic surfactants can include salts (including, for example, sodium, potassium, ammonium, and substituted ammonium salts such as mono-, di- and triethanolamine salts) of soap, $C_6$-$C_{20}$ linear alkylbenzenesulfonates, $C_6$-$C_{22}$ primary or secondary alkanesulfonates, $C_6$-$C_{24}$ olefinsulfonates, sulfonated polycarboxylic acids prepared by sulfonation of the pyrolyzed product of alkaline earth metal citrates, $C_6$-$C_{24}$ alkylpolyglycolethersulfates, alkyl ester sulfates such as $C_{14-16}$ methyl ester sulfates; acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinate (especially saturated and unsaturated $C_{12}$-$C_{18}$ monoesters) diesters of sulfosuccinate (especially saturated and unsaturated $C_6$-$C_{14}$ diesters), acyl sarcosinates, sulfates of alkylpolysaccharides such as the sulfates of alkylpolyglucoside, branched primary alkyl sulfates, alkyl polyethoxy carboxylates such as those of the formula $RO(CH_2CH_2O)_kCH_2COO^-M^+$ wherein R is a $C_8$-$C_{22}$ alkyl, k is an integer from 0 to 10, and M is a soluble salt-forming cation. Examples of the foregoing anionic surfactants are available under the following tradenames: Rhodapon®, Stepanol®, Hostapur®, Surfine®, Sandopan®, Neodox®, Biosoft®, and Avanel®.

Preferably the anionic surfactant constituent necessarily includes one or more anionic surfactants based on alkyl sulfates or alkyl sulfonates, and further preferably such are present to the exclusion of other anionic surfactants. Yet more preferably the anionic surfactant constituents comprises one or more anionic surfactants based on secondary alkyl sulfonates, and especially preferably to the exclusion of other anionic surfactants.

The anionic surfactant may be present in any effective amount, and advantageously is present in an amount of up to about 5% wt, preferably from about 0.001-4% wt., yet more preferably between about 0.25-3% wt. based on the total weight of the hard surface treatment composition of which it forms a part.

The present inventors have surprisingly found that the selection of the anionic surfactant plays a critical role in the antimicrobial efficacy of the hard surface treatment compositions which also include lactic acid in the organic acid constituent. Namely, the inventors have found that the combination of the preferred anionic surfactants especially anionic surfactants based on alkyl sulfonates, and especially those based on secondary alkyl sulfonates appear to provide a synergistic benefit in improving the overall antimicrobial efficacy of the treatment compositions. Thus, the combination of alkyl sulfonates, and especially those based on secondary alkyl sulfonates with lactic acid, such as in the proportions (ratios) and amounts described herein and particularly with reference to one or more of the examples permits for the formulation of hard surface treatment compositions which have reduced amounts of organic acids, especially reduced amounts of lactic acid while providing comparable antimicrobial efficacy as compared to commercial preparations which appear to require an increased amount of organic acids, viz., lactic acid, in order to provide comparable antimicrobial efficacy. Such antimicrobial efficacy permits for the provision of hard surface treatment compositions which provide a sanitizing and/or disinfecting benefit without requiring higher amounts of acid.

The hard surface treatment compositions of the invention also include a nonionic surfactant constituent which includes one or more nonionic surfactants.

One class of exemplary useful nonionic surfactants are polyethylene oxide condensates of alkyl phenols. These compounds include the condensation products of alkyl phenols having an alkyl group containing from about 6 to 12 carbon atoms in either a straight chain or branched chain configuration with ethylene oxide, the ethylene oxide being present in an amount equal to 5 to 25 moles of ethylene oxide per mole of alkyl phenol. The alkyl substituent in such compounds can be derived, for example, from polymerized propylene, diisobutylene and the like. Examples of compounds of this type include nonyl phenol condensed with about 9.5 moles of ethylene oxide per mole of nonyl phenol; dodecylphenol condensed with about 12 moles of ethylene oxide per mole of phenol; dinonyl phenol condensed with about 15 moles of ethylene oxide per mole of phenol and diisooctyl phenol condensed with about 15 moles of ethylene oxide per mole of phenol.

Further useful nonionic surfactants include the condensation products of aliphatic alcohols with from about 1 to about 60 moles of ethylene oxide. The alkyl chain of the aliphatic alcohol can either be straight or branched, primary or secondary, and generally contains from about 8 to about 22 carbon atoms. Examples of such ethoxylated alcohols include the condensation product of myristyl alcohol condensed with about 10 moles of ethylene oxide per mole of alcohol and the condensation product of about 9 moles of ethylene oxide with coconut alcohol (a mixture of fatty alcohols with alkyl chains varying in length from about 10 to 14 carbon atoms). Other examples are those $C_6$-$C_{11}$ straight-chain alcohols which are ethoxylated with from about 3 to about 6 moles of ethylene oxide. Their derivation is well known in the art. Examples include Alfonic® 810-4.5 (also available as Teric G9A5), which is described in product literature from Sasol as a $C_{8-10}$ having an average molecular weight of 356, an ethylene oxide content of about 4.85 moles (about 60 wt. %), and an HLB of about 12; Alfonic® 810-2, which is described in product literature from Sasol as a $C_{8-10}$ having an average molecular weight of 242, an ethylene oxide content of about 2.1 moles (about 40 wt. %), and an HLB of about 12; and Alfonic® 610-3.5, which is described in product literature from Sasol as having an average molecular weight of 276, an ethylene oxide content of about 3.1 moles (about 50 wt. %), and an HLB of 10. Product literature from Sasol also identifies that the numbers in the alcohol ethoxylate name designate the carbon chain length (numbers before the hyphen) and the average moles of ethylene oxide (numbers after the hyphen) in the product.

Further exemplary useful nonionic surfactants include ethoxylated available from Shell Chemical Company which are described as $C_9$-$C_{11}$ ethoxylated alcohols and marketed under the Neodol® tradename. The Neodol® 91 series nonionic surfactants of interest include Neodol 91-2.5, Neodol 91-6, and Neodol 91-8. Neodol 91-2.5 has been described as having about 2.5 ethoxy groups per molecule; Neodol 91-6 has been described as having about 6 ethoxy groups per molecule; and Neodol 91-8 has been described as having about 8 ethoxy groups per molecule. Still further examples of ethoxylated alcohols include the Rhodasurf® DA series nonionic surfactants available from Rhodia which are described to be branched isodecyl alcohol ethoxylates. Rhodasurf DA-530 has been described as having 4 moles of ethoxylation and an HLB of 10.5; Rhodasurf DA-630 has been described as having 6 moles of ethoxylation with an HLB of 12.5; and Rhodasurf DA-639 is a 90% solution of DA-630.

Further examples of ethoxylated alcohols include those from Tomah Products (Milton, Wis.) under the Tomadol tradename with the formula $RO(CH_2CH_2O)_nH$ where R is the primary linear alcohol and n is the total number of moles of ethylene oxide. The ethoxylated alcohol series from Tomah include 91-2.5; 91-6; 91-8—where R is linear C9/C10/C11 and n is 2.5, 6, or 8; 1-3; 1-5; 1-7; 1-73B; 1-9; —where R is linear C11 and n is 3, 5, 7 or 9; 23-1; 23-3; 23-5; 23-6.5—where R is linear C12/C13 and n is 1, 3, 5, or 6.5; 25-3; 25-7; 25-9; 25-12—where R is linear C12/C13 C14/C15 and n is 3, 7, 9, or 12; and 45-7; 45-13—where R is linear C14/C15 and n is 7 or 13.

Other examples of useful nonionic surfactants include those having a formula $RO(CH_2CH_2O)_nH$ wherein R is a mixture of linear, even carbon-number hydrocarbon chains ranging from $C_{12}H_{25}$ to $C_{16}H_{33}$ and n represents the number of repeating units and is a number of from about 1 to about 12. Surfactants of this formula are presently marketed under the Genapol® tradename. available from Clariant, Charlotte, N.C., include the 26-L series of the general formula $RO(CH_2CH_2O)_nH$ wherein R is a mixture of linear, even carbon-number hydrocarbon chains ranging from $C_{12}H_{25}$ to $C_{16}H_{33}$ and n represents the number of repeating units and is a number of from 1 to about 12, such as 26-L-1,26-L-1,6,26-L-2,26-L-3,26-L-5,26-L-45, 26-L-50, 26-L-60, 26-L-60N, 26-L-75, 26-L-80, 26-L-98N, and the 24-L series, derived from synthetic sources and typically contain about 55% $C_{12}$ and 45% $C_{1-4}$ alcohols, such as 24-L-3,24-L-45, 24-L-50, 24-L-60, 24-L-60N, 24-L-75, 24-L-92, and 24-L-98N. From product literature, the single number following the "L" corresponds to the average degree of ethoxylation (numbers between 1 and 5) and the two digit number following the letter "L" corresponds to the cloud point in ° C. of a 1.0 wt. % solution in water.

A further class of nonionic surfactants which are contemplated to be useful include those based on alkoxy block copolymers, and in particular, compounds based on ethoxy/propoxy block copolymers. Polymeric alkylene oxide block copolymers include nonionic surfactants in which the major portion of the molecule is made up of block polymeric $C_2$-$C_4$ alkylene oxides. Such nonionic surfactants, while preferably built up from an alkylene oxide chain starting group, and can have as a starting nucleus almost any active hydrogen containing group including, without limitation, amides, phenols, thiols and secondary alcohols.

One further group of such useful nonionic surfactants containing the characteristic alkylene oxide blocks are those which may be generally represented by the formula (A):

$$HO\text{-}(EO)_x(PO)_y(EO)_z\text{—}H \quad (A)$$

where

EO represents ethylene oxide,

PO represents propylene oxide, y equals at least 15, $(EO)_{x+y}$ equals 20 to 50% of the total weight of said compounds, and, the total molecular weight is preferably in the range of about 2000 to 15,000. These surfactants are available under the PLURONIC tradename from BASF or Emulgen from Kao.

Another group of nonionic surfactants appropriate for use in the new compositions can be represented by the formula (B):

$$R\text{-}(EO,PO)_a(EO,PO)_b\text{—}H \quad (B)$$

wherein R is an alkyl, aryl or aralkyl group, where the R group contains 1 to 20 carbon atoms, the weight percent of EO is within the range of 0 to 45% in one of the blocks a, b, and within the range of 60 to 100% in the other of the blocks a, b, and the total number of moles of combined EO and PO is in the range of 6 to 125 moles, with 1 to 50 moles in the PO rich block and 5 to 100 moles in the EO rich block.

Further nonionic surfactants which in general are encompassed by Formula B include butoxy derivatives of propylene oxide/ethylene oxide block polymers having molecular weights within the range of about 2000-5000.

Still further useful nonionic surfactants containing polymeric butoxy (BO) groups can be represented by formula (C) as follows:

$$RO\text{—}(BO)_n(EO)_x\text{—}H \quad (C)$$

wherein R is an alkyl group containing Ito 20 carbon atoms, n is about 5-15 and x is about 5-15.

Also useful as the nonionic block copolymer surfactants, which also include polymeric butoxy groups, are those which may be represented by the following formula (D):

$$HO\text{-}(EO)_x(BO)_n(EO)_y\text{—}H \quad (D)$$

wherein n is about 5-15, preferably about 15, x is about 5-15, preferably about 15, and y is about 5-15, preferably about 15.

Still further useful nonionic block copolymer surfactants include ethoxylated derivatives of propoxylated ethylene diamine, which may be represented by the following formula:

(E)

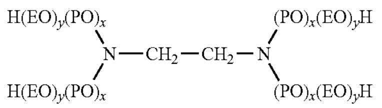

where (EO) represents ethoxy, (PO) represents propoxy, the amount of $(PO)_x$ is such as to provide a molecular weight prior to ethoxylation of about 300 to 7500, and the amount of $(EO)_y$ is such as to provide about 20% to 90% of the total weight of said compound.

A particularly useful, and preferred class of nonionic surfactants are monobranched alkoxylated C10-fatty alcohols and/or C11-fatty alcohols; these are jointly referred to as C10/C11-fatty alcohols. These materials are nonionic surfactants are monobranched and may have various degrees of alkoxylation, and are typically ethoxylated with between about 3 and 14 moles of ethylene oxide, typically 4, 5, 6, 7, 8, 9, 10 or 14 moles ethylene oxide. Such nonionic surfactants are presently commercially available under the Lutensol® (ex. BASF AG) and are available in a variety of grades e.g., Lutensol® XL 40 recited by its supplier to be a C10-Guerbet alcohol which is approximately 4 moles of ethoxylation, Lutensol® XL 50 recited by its supplier to be a C10-Guerbet alcohol which is approximately 5 moles of ethoxylation, Lutensol® XL 60 recited by its supplier to be a C10-Guerbet alcohol which is approximately 6 moles of ethoxylation, Lutensol® XL 70 recited by its supplier to be a C10-Guerbet alcohol which is approximately 7 moles of ethoxylation, Lutensol® XL 40 recited by its supplier to be a C10-Guerbet alcohol which is approximately 4 moles of ethoxylation, Lutensol® XL 79 recited by its supplier to be a C10-Guerbet alcohol which is approximately 7 moles of ethoxylation, Lutensol® XL 80 recited by its supplier to be a C10-Guerbet alcohol which is approximately 8 moles of ethoxylation, Lutensol® XL 89 recited by its supplier to be a C10-Guerbet alcohol which is approximately 8 moles of ethoxylation, Lutensol® XL 90 recited by its supplier to be a C10-Guerbet alcohol which is approximately 9 moles of ethoxylation, Lutensol® XL 99 recited by its supplier to be a C10-Guerbet alcohol which is approximately 9 moles of ethoxylation, Lutensol® XL 100 recited by its supplier to be a C10-Guerbet alcohol which is approximately 10 moles of ethoxylation, Lutensol® XL 140 recited by its supplier to be a C10-Guerbet alcohol which is approximately 14 moles of ethoxylation, all available from BASF AG. Alternately or additionally, nonionic surfactant based on monobranched alkoxylated C10-fatty alcohols marketed under the Lutensol® XP series of surfactants, also ex. BASF AG, may also be used. By way of non-limiting example such include: Lutensol® XP 30 recited by its supplier to be a C10-Guerbet alcohol which is approximately 3 moles of ethoxylation; Lutensol® XP 40 recited by its supplier to be a C10-Guerbet alcohol which is approximately 4 moles of ethoxylation; Lutensol® XP 50 recited by its supplier to be a C10-Guerbet alcohol which is approximately 5 moles of ethoxylation; Lutensol® XP 60 recited by its supplier to be a C10-Guerbet alcohol which is approximately 6 moles of ethoxylation; Lutensol® XP 70 recited by its supplier to be a C10-Guerbet alcohol which is approximately 7 moles of ethoxylation; Lutensol® XP 79 recited by its supplier to be a C10-Guerbet alcohol which is approximately 7 moles of ethoxylation; Lutensol® XP 80 recited by its supplier to be a C10-Guerbet alcohol which is approximately 8 moles of ethoxylation; Lutensol® XP 89 recited by its supplier to be a C10-Guerbet alcohol which is approximately 8 moles of ethoxylation; Lutensol® XP 90 recited by its supplier to be a C10-Guerbet alcohol which is approximately 9 moles of ethoxylation; Lutensol® XP 99 recited by its supplier to be a C10-Guerbet alcohol which is approximately 9 moles of ethoxylation; Lutensol® XP 100 recited by its supplier to be a C10-Guerbet alcohol which is approximately 10 moles of ethoxylation; and Lutensol® XP 140 recited by its supplier to be a C10-Guerbet alcohol which is approximately 14 moles of ethoxylation.

While the foregoing materials are ethoxylated, it is to be understood that other alkoxylated, e.g., propoxylated, butoxylated, as well as mixed ethoxylated and propoxylated branched nonionic alkyl polyethylene glycol ether may also be used.

It is contemplated by the inventors that similar nonionic surfactants based on monobranched alkoxylated C11-fatty alcohols may be used to substitute part of, or all of the nonionic surfactant based on monobranched alkoxylated C10-fatty alcohols. These include for example, the Genapol® UD series described as tradenames Genapol® UD 030, $C_{11}$-oxo-alcohol polyglycol ether with 3 EO; Genapol® UD, 050 $C_{11}$-oxo-alcohol polyglycol ether with 5 EO; Genapol® UD 070, $C_{11}$-oxo-alcohol polyglycol ether with 7 EO; Genapol® UD 080, $C_{11}$-oxo-alcohol polyglycol ether with 8 EO; Genapol® UD 088, $C_{11}$-oxo-alcohol polyglycol ether with 8 EO; and Genapol® UD 110, $C_{11}$-oxo-alcohol polyglycol ether with 11 EO (ex. Clariant).

The nonionic surfactant based on monobranched alkoxylated C10/C11-fatty alcohols (and/or C11-fatty alcohols) is often advantageously present in the hard surface cleaning compositions.

In certain particularly preferred embodiment, at least one monobranched alkoxylated C10/C11-fatty alcohol, preferably based on a C-10 Guerbet alcohol is necessarily present in the inventive compositions.

Further useful nonionic surfactants include alkylpolyglucosides. These materials may also be referred to as alkyl monoglucosides and alkylpolyglucosides. Suitable alkyl polyglucosides are known nonionic surfactants which are alkaline and electrolyte stable. Such include alkyl glucosides, alkyl polyglucosides and mixtures thereof. Alkyl glucosides and alkyl polyglucosides can be broadly defined as condensation articles of long chain alcohols, e.g., $C_8$-$C_{30}$ alcohols, with sugars or starches or sugar or starch polymers i.e., glucosides or polyglucosides. These compounds can be represented by the formula $(S)_n$—O—R wherein S is a sugar moiety such as glucose, fructose, mannose, and galactose; n is an integer of from about 1 to about 1000, and R is a $C_{8-30}$ alkyl group. Examples of long chain alcohols from which the alkyl group can be derived include decyl alcohol, cetyl alcohol, stearyl alcohol, lauryl alcohol, myristyl alcohol, oleyl alcohol and the like.

Alkyl mono- and polyglucosides are prepared generally by reacting a monosaccharide, or a compound hydrolyzable to a monosaccharide with an alcohol such as a fatty alcohol in an acid medium. Various glucoside and polyglucoside compounds including alkoxylated glucosides and processes for making them are disclosed in U.S. Pat. No. 2,974,134; U.S. Pat. No. 3,219,656; U.S. Pat. No. 3,598,865; U.S. Pat. No. 3,640,998; U.S. Pat. No. 3,707,535; U.S. Pat. No. 3,772,269; U.S. Pat. No. 3,839,318; U.S. Pat. No. 3,974,138; U.S. Pat. No. 4,223,129; and U.S. Pat. No. 4,528,106.

Exemplary useful alkyl glucoside surfactants suitable for use in the practice of this invention may be represented by formula I below:

$$RO—(R_1O)_y\text{-}(G)_xZ_b, \qquad \text{I}$$

wherein:

R is a monovalent organic radical containing from about 6 to about 30, preferably from about 8 to about 18 carbon atoms;

$R_1$ is a divalent hydrocarbon radical containing from about 2 to about 4 carbon atoms;

O is an oxygen atom;

y is a number which has an average value from about 0 to about 1 and is preferably 0;

G is a moiety derived from a reducing saccharide containing 5 or 6 carbon atoms; and x is a number having an average value from about 1 to 5 (preferably from 1.1 to 2);

Z is $O_2M^1$,

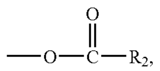

$O(CH_2)$, $CO_2M^1$, $OSO_3M^1$, or $O(CH_2)SO_3M^1$; $R_2$ is $(CH_2)CO_2M^1$ or $CH{=}CHCO_2M^1$; (with the proviso that Z can be $O_2M^1$ only if Z is in place of a primary hydroxyl group in which the primary hydroxyl-bearing carbon atom, —$CH_2OH$, is oxidized to form a

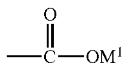

group);

b is a number of from 0 to 3x+1 preferably an average of from 0.5 to 2 per glycosal group;

p is 1 to 10, $M^1$ is $H^+$ or an organic or inorganic cation, such as, for example, an alkali metal, ammonium, monoethanolamine, or calcium.

As defined in Formula I above, R is generally the residue of a fatty alcohol having from about 8 to 30 and preferably 8 to 18 carbon atoms.

Further exemplary useful alkylpolyglucosides include those according to the formula II:

$$R_2O-(C_nH_{2n}O)_r-(Z)_x \quad \text{II}$$

wherein:

$R_2$ is a hydrophobic group selected from alkyl groups, alkylphenyl groups, hydroxyalkylphenyl groups as well as mixtures thereof, wherein the alkyl groups may be straight chained or branched, and which contain from about 8 to about 18 carbon atoms, n has a value of 2-8, especially a value of 2 or 3; r is an integer from 0 to 10, but is preferably 0, Z is derived from glucose; and, x is a value from about 1 to 8, preferably from about 1.5 to 5.

Preferably the alkylpolyglucosides are nonionic fatty alkylpolyglucosides which contain a straight chain or branched chain $C_8$-$C_{15}$ alkyl group, and have an average of from about 1 to 5 glucose units per fatty alkylpolyglucoside molecule. More preferably, the nonionic fatty alkylpolyglucosides which contain straight chain or branched $C_8$-$C_{15}$ alkyl group, and have an average of from about 1 to about 2 glucose units per fatty alkylpolyglucoside molecule.

Examples of such alkylpolyglucosides as described above include, for example, APG™ 325 which is described as being a $C_9$-$C_{11}$ alkyl polyglucoside, also commonly referred to as D-glucopyranoside, (ex. Cognis). Further exemplary alkylpolyglucosides include Glucopon® 625 CS which is described as being a $C_{10}$-$C_{16}$ alkyl polyglucoside, also commonly referred to as a D-glucopyranoside, (ex. Cognis), lauryl polyglucoside available as APG™ 600 CS and 625 CS (ex. Cognis) as well as other materials sold under the Glucopon® tradename, e.g., Glucopon® 215, Glucopon® 225, Glucopon® 425, and Glucopon® 425N, especially one or more of the alkyl polyglucosides demonstrated in one or more of the examples. It is believed that the alkylpolyglucoside surfactants sold under the Glucopon® tradename are synthezied at least in part on synthetically produced starting constituents and are colorless or only slightly colored, while those sold under the APG™ are synthesized at least in part on naturally occurring or sourced starting constituents and are more colored in appearance.

In certain preferred embodiments the nonionic surfactant constituent necessarily includes one or more alkylpolyglucosides, such as those currently being sold under the Glucopon® or APG™ tradenames.

In certain particularly preferred embodiments the sole nonionic surfactants present are those based on monobranched alkoxylated C10/C11-fatty alcohol, preferably based on a C-10 Guerbet alcohol, concurrently with an alkylpolyglucoside, to the exclusion of other nonionic surfactants.

The nonionic surfactant constituent may be present in any effective amount, and advantageously is present in an amount of up to about 5% wt, preferably from about 0.001-4% wt., yet more preferably between about 0.25-3% wt. based on the total weight of the hard surface treatment composition of which it forms a part.

Optionally, the hard surface treatment compositions may include one or more cosurfactants in addition to the anionic surfactant constituent and the nonionic surfactant constituent. Such include amphoteric and zwitterionic surfactants, and less preferably may also include one or more cationic surfactants.

Exemplary cosurfactants include amine oxides such as:

alkyl di($C_1$-$C_7$) amine oxides in which the alkyl group has about 10-20, and preferably 12-16 carbon atoms, and can be straight or branched chain, saturated or unsaturated. Examples of such compounds include lauryl dimethyl amine oxide, myristyl dimethyl amine oxide, and those in which the alkyl group is a mixture of different amine oxide, dimethyl cocoamine oxide, dimethyl (hydrogenated tallow) amine oxide, and myristyl/palmityl dimethyl amine oxide;

alkyl di(hydroxy $C_1$-$C_7$) amine oxides in which the alkyl group has about 10-20, and preferably 12-16 carbon atoms, and can be straight or branched chain, saturated or unsaturated. Examples of such compounds include bis(2-hydroxyethyl) cocoamine oxide, bis(2-hydroxyethyl) tallowamine oxide; and bis(2-hydroxyethyl) stearylamine oxide;

alkylamidopropyl di($C_1$-$C_7$) amine oxides in which the alkyl group has about 10-20, and preferably 12-16 carbon atoms, and can be straight or branched chain, saturated or unsaturated. Examples of such compounds include cocoamidopropyl dimethyl amine oxide and tallowamidopropyl dimethyl amine oxide; and alkylmorpholine oxides in which the alkyl group has about 10-20, and preferably 12-16 carbon atoms, and can be straight or branched chain, saturated or unsaturated.

Non-limiting examples of exemplary amphoteric surfactants which are contemplated to be useful in the cosurfactant constituent include one or more water-soluble betaine surfactants which may be represented by the general formula:

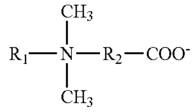

wherein $R_1$ is an alkyl group containing from 8 to 18 carbon atoms, or the amido radical which may be represented by the following general formula:

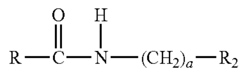

wherein R is an alkyl group having from 8 to 18 carbon atoms, a is an integer having a value of from 1 to 4 inclusive, and $R_2$ is a $C_1$-$C_4$ alkylene group. Examples of such water-soluble betaine surfactants include dodecyl dimethyl betaine, as well as cocoamidopropylbetaine.

When present, any cosurfactant(s) may be present in any cleaning effective amounts up to about 5% wt, preferably are present in amounts of from about 0.01-5% wt., yet more preferably from about 0.01-2.5% wt., based on the total weight of the composition of which it forms a part.

As is noted above, the compositions according to the invention are largely aqueous in nature. Water is added to order to provide to 100% by weight of the compositions of the invention. The water may be tap water, but is preferably distilled and is most preferably deionized water. If the water is tap water, it is preferably substantially free of any undesirable impurities such as organics or inorganics, especially minerals salts which are present in hard water which may thus undesirably interfere with the operation of the constituents present in the aqueous compositions according to the invention. Preferably at least 80% wt, more preferably at least 85% wt, and most preferably at least about 90% wt of the compositions are water.

The inventive compositions may optionally include one or more one or more further constituents useful in improving one or more aesthetic characteristics or the compositions or in improving one or more technical characteristics of the compositions. Exemplary further optional constituents include coloring agents, fragrances and fragrance solubilizers, viscosity modifying agents including one or more thickeners, pH adjusting agents and pH buffers including organic and inorganic salts, optical brighteners, opacifying agents, hydrotropes, abrasives, and preservatives, as well as other optional constituents providing improved technical or aesthetic characteristics known to the relevant art. When present, the total amount of such one or more optional constituents present in the inventive compositions do not exceed about 10% wt., preferably do not exceed 5% wt., and most preferably do not exceed 2.5% wt.

By way of non-limiting example pH adjusting agents include phosphorus containing compounds, monovalent and polyvalent salts such as of silicates, carbonates, and borates, certain acids and bases, tartrates and certain acetates. Further exemplary pH adjusting agents include mineral acids, basic compositions, and organic acids, which are typically required in only minor amounts. By way of further non-limiting example pH buffering compositions include the alkali metal phosphates, polyphosphates, pyrophosphates, triphosphates, tetraphosphates, silicates, metasilicates, polysilicates, carbonates, hydroxides, and mixtures of the same. Certain salts, such as the alkaline earth phosphates, carbonates, hydroxides, can also function as buffers. It may also be suitable to use as buffers such materials as aluminosilicates (zeolites), borates, aluminates and certain organic materials such as gluconates, succinates, maleates, and their alkali metal salts. When present, the pH adjusting agent, especially the pH buffers are present in an amount effective in order to maintain the pH of the inventive composition within a target pH range. Hydroxides, such as sodium hydroxide may be advantageously used.

The inventive compositions may include one or more coloring agents which may be included to impart a desired color or tint to the compositions.

The compositions of the invention optionally but in certain cases desirably include a fragrance constituent. Fragrance raw materials may be divided into three main groups: (1) the essential oils and products isolated from these oils; (2) products of animal origin; and (3) synthetic chemicals.

The essential oils consist of complex mixtures of volatile liquid and solid chemicals found in various parts of plants. Mention may be made of oils found in flowers, e.g., jasmine, rose, mimosa, and orange blossom; flowers and leaves, e.g., lavender and rosemary; leaves and stems, e.g., geranium, patchouli, and petitgrain; barks, e.g., cinnamon; woods, e.g., sandalwood and rosewood; roots, e.g., angelica; rhizomes, e.g., ginger; fruits, e.g., orange, lemon, and bergamot; seeds, e.g., aniseed and nutmeg; and resinous exudations, e.g., myrrh. These essential oils consist of a complex mixture of chemicals, the major portion thereof being terpenes, including hydrocarbons of the formula $(C_5H_8)_n$ and their oxygenated derivatives. Hydrocarbons such as these give rise to a large number of oxygenated derivatives, e.g., alcohols and their esters, aldehydes and ketones. Some of the more important of these are geraniol, citronellol and terpineol, citral and citronellal, and camphor. Other constituents include aliphatic aldehydes and also aromatic compounds including phenols such as eugenol. In some instances, specific compounds may be isolated from the essential oils, usually by distillation in a commercially pure state, for example, geraniol and citronellal from citronella oil; citral from lemon-grass oil; eugenol from clove oil; linalool from rosewood oil; and safrole from sassafras oil. The natural isolates may also be chemically modified as in the case of citronellal to hydroxy citronellal, citral to ionone, eugenol to vanillin, linalool to linalyl acetate, and safrol to heliotropin.

Animal products used in perfumes include musk, ambergris, civet and castoreum, and are generally provided as alcoholic tinctures.

The synthetic chemicals include not only the synthetically made, also naturally occurring isolates mentioned above, but also include their derivatives and compounds unknown in nature, e.g., isoamylsalicylate, amylcinnamic aldehyde, cyclamen aldehyde, heliotropin, ionone, phenylethyl alcohol, terpineol, undecalactone, and gamma nonyl lactone.

Fragrance compositions as received from a supplier may be provided as an aqueous or organically solvated composition, and may include as a hydrotrope or emulsifier a surface-active agent, typically a surfactant, in minor amount. Such fragrance compositions are quite usually proprietary blends of many different specific fragrance compounds. However, one of ordinary skill in the art, by routine experimentation, may easily determine whether such a proprietary fragrance composition is compatible in the compositions of the present invention.

One or more coloring agents may also be used in the inventive compositions in order to impart a desired colored appearance or colored tint to the compositions. Known art water soluble or water dispersible pigments and dyes may be added in effective amounts.

A further optional constituent are one or more preservatives, although such are not normally expected to be necessary due to the antimicrobial properties of the hard surface treatment compositions. Such preservatives are primarily included to reduce the growth of undesired microorganisms within the composition during storage prior to use. Exemplary useful preservatives include compositions which include parabens, including methyl parabens and ethyl parabens, glutaraldehyde, formaldehyde, 2-bromo-2-nitropropoane-1,3-diol, 5-chloro-2-methyl-4-isothiazolin-3-one, 2-methyl-4-isothiazoline-3-one, and mixtures thereof. One exemplary composition is a combination 5-chloro-2-methyl-4-isothiazolin-3-one and 2-methyl-4-isothiazolin-3-one where the amount of either component may be present in the mixture anywhere from 0.001 to 99.99 weight percent, based on the total amount of the preservative. Further exemplary useful preservatives include those which are commercially including a mixture of 5-chloro-2-methyl-4-isothiazolin-3-one and 2-methyl-4-isothiazolin-3-one marketed under the trademark KATHON® CG/ICP as a preservative composition presently commercially available from Rohm and Haas (Philadelphia, Pa.). Further useful and commercially available preservative compositions include KATHON® CG/ICP II, a further preservative composition presently commercially available from Rohm and Haas (Philadelphia, Pa.), PROXEL® which is presently commercially available from Zeneca Biocides (Wilmington, Del.), SUTTOCIDE® A which is presently commercially available from Sutton Laboratories (Chatam, N.J.) as well as TEXTAMER® 38AD which is presently commercially available from Calgon Corp. (Pittsburgh, Pa.).

The inventive compositions may include a thickener constituent which may be added in any effective amount in order to increase the viscosity of the compositions. Exemplary thickeners useful in the thickener constituent include one or more of polysaccharide polymers selected from cellulose, alkyl celluloses, alkoxy celluloses, hydroxy alkyl celluloses, alkyl hydroxy alkyl celluloses, carboxy alkyl celluloses, carboxy alkyl hydroxy alkyl celluloses, naturally occurring polysaccharide polymers such as xanthan gum, guar gum, locust bean gum, tragacanth gum, or derivatives thereof, polycarboxylate polymers, polyacrylamides, clays, and mixtures thereof.

Examples of the cellulose derivatives include methyl cellulose ethyl cellulose, hydroxymethyl cellulose hydroxy ethyl cellulose, hydroxy propyl cellulose, carboxy methyl cellulose, carboxy methyl hydroxyethyl cellulose, hydroxypropyl cellulose, hydroxy propyl methyl cellulose, ethylhydroxymethyl cellulose and ethyl hydroxy ethyl cellulose.

Exemplary polycarboxylate polymers thickeners have a molecular weight from about 500,000 to about 4,000,000, preferably from about 1,000,000 to about 4,000,000, with, preferably, from about 0.5% to about 4% crosslinking. Preferred polycarboxylate polymers include polyacrylate polymers including those sold under trade names Carbopol®, Acrysol® ICS-1 and Sokalan®. The preferred polymers are polyacrylates. Other monomers besides acrylic acid can be used to form these polymers including such monomers as ethylene and propylene which act as diluents, and maleic anhydride which acts as a source of additional carboxylic groups.

Exemplary clay thickeners comprise, for example, colloid-forming clays, for example, such as smectite and attapulgite types of clay thickeners. The clay materials can be described as expandable layered clays, i.e., aluminosilicates and magnesium silicates. The term "expandable" as used to describe the instant clays relates to the ability of the layered clay structure to be swollen, or expanded, on contact with water. The expandable clays used herein are those materials classified geologically as smectites (or montmorillonite) and attapulgites (or polygorskites).

When used, preferred thickeners are those which provide a useful viscosity increasing benefit at the ultimate pH of the compositions, particularly thickeners which are useful at pH's of about 3.5 or less. While in certain embodiments the compositions may comprise a thicker constituent, it is generally preferred the compositions exhibit viscosities similar to that of water. The compositions preferably have a viscosity of not more than about 50 cps at room temperature, more preferably have a viscosity of not more than about 30 cps at room temperature, and most preferably have a viscosity of not more than about 15 cps at room temperature.

The compositions according to the invention are desirably provided as a ready to use product which may be directly applied to a hard surface. Hard surfaces which are to be particularly denoted are lavatory fixtures, lavatory appliances (toilets, bidets, shower stalls, bathtubs and bathing appliances), wall and flooring surfaces especially those which include refractory materials and the like. Further hard surfaces which are particularly denoted are those associated with dishwashers, kitchen environments and other environments associated with food preparation. Hard surfaces which are those associated with hospital environments, medical laboratories and medical treatment environments. Such hard surfaces described above are to be understood as being recited by way of illustration and not be way of limitation.

The inventive compositions may be packaged in any suitable container particularly flasks or bottles, including squeeze-type bottles, as well as bottles provided with a spray apparatus which is used to dispense the composition by spraying. The inventive compositions are readily pourable and readily pumpable cleaning compositions which features the benefits described above. Accordingly the inventive compositions are desirably provided as a ready to use product in a manually operated spray dispensing container, or may be supplied in aerosolized product wherein it is discharged from a pressurized aerosol container. Propellants which may be used are well known and conventional in the art and include, for example, a hydrocarbon, of from 1 to 10 carbon atoms, such as n-propane, n-butane, isobutane, n-pentane, isopentane, and mixtures thereof; dimethyl ether and blends thereof as well as individual or mixtures of chloro-, chlorofluoro- and/or fluorohydrocarbons- and/or hydrochlorofluorocarbons (HCFCs). Useful commercially available compositions include A-70 (Aerosol compositions with a vapor pressure of 70 psig available from companies such as Diversified and Aeropress) and Dymel® 152a (1,1-difluoroethane from DuPont). Compressed gases such as carbon dioxide, compressed air, nitrogen, and possibly dense or supercritical fluids may also be used. In such an application, the composition is dispensed by activating the release nozzle of said aerosol type container onto the area in need of treatment, and in accordance with a manner as above-described the area is treated (e.g., cleaned and/or sanitized and/or disinfected). If a propellant is used, it will generally be in an amount of from about 1% to about 50% of the aerosol formulation with preferred amounts being from about 2% to about 25%, more preferably from about 5% to about 15%. Generally speaking, the amount of a particular propellant employed should provide an internal pressure of from about 20 to about 150 psig at 70° F.

The compositions according to the invention can also be suited for use in a consumer "spray and wipe" application as a cleaning composition. In such an application, the consumer generally applies an effective amount of the composition using the pump and within a few moments thereafter, wipes off the treated area with a rag, towel, or sponge, usually a disposable paper towel or sponge. In certain applications, however, especially where undesirable stain deposits are heavy, the cleaning composition according to the invention may be left on the stained area until it has effectively loosened the stain deposits after which it may then be wiped off, rinsed off, or otherwise removed. For particularly heavy deposits of such undesired stains, multiple applications may also be used. Optionally, after the composition has remained on the surface for a period of time, it could be rinsed or wiped from the surface.

It is contemplated that certain preferred embodiments of inventive formulations may also provide a disinfecting or sanitizing benefit to hard surfaces wherein the presence of undesired microorganisms are suspected such as gram positive or gram negative bacteria. This is due to the low pH of particularly preferred embodiments of the invention, particularly wherein the compositions are at a pH of 3.5 or less.

Also provided is a method for the treatment of hard surfaces wherein the presence of such undesired microorganisms are suspected which method includes the step of applying a disinfecting or sanitizing effective amount of a composition described herein.

Whereas the compositions of the present invention are intended to be used in the types of liquid forms described, nothing in this specification shall be understood as to limit the use of the composition according to the invention with a further amount of water to form a cleaning solution therefrom. In such a proposed diluted cleaning solution, the greater the proportion of water added to form said cleaning dilution will, the greater may be the reduction of the rate and/or efficacy of the thus formed cleaning solution. Accordingly, longer residence times upon the stain to effect their loosening and/or the usage of greater amounts may be necessitated. Conversely, nothing in the specification shall be also understood to limit the forming of a "super-concentrated" cleaning composition based upon the composition described above. Such a super-concentrated ingredient composition is essentially the same as the cleaning compositions described above except in that they include a lesser amount of water.

The composition of the present invention, whether as described herein or in a concentrate or super concentrate form, can also be applied to a hard surface by the use of a carrier substrate. One example of a useful carrier substrate is a wet wipe. The wipe can be of a woven or non-woven nature. Fabric substrates can include nonwoven or woven pouches, sponges including both closed cell and open celled sponges, including sponges formed from celluloses as well as other polymeric material, as well as in the form of abrasive or non-abrasive cleaning pads. Such fabrics are known commercially in this field and are often referred to as wipes. Such substrates can be resin bonded, hydroentangled, thermally bonded, meltblown, needlepunched, or any combination of the former. The carrier substrate useful with the present inventive compositions may also be a wipe which includes a film forming substrate such as a water soluble polymer. Such self-supporting film substrates may be sandwiched between layers of fabric substrates and heat sealed to form a useful substrate.

The compositions of the present invention are advantageously absorbed onto the carrier substrate, i.e., a wipe to form a saturated wipe. The wipe can then be sealed individually in a pouch which can then be opened when needed or a multitude of wipes can be placed in a container for use on an as needed basis. The container, when closed, sufficiently sealed to prevent evaporation of any components from the compositions. In use, a wipe is removed from the container and then wiped across an area in need of treatment; in case of difficult to treat stains the wipe may be re-wiped across the area in need of treatment, or a plurality of saturated wipes may also be used. Certain embodiments of the invention, including certain particularly preferred embodiments of the invention are disclosed in the following examples.

EXAMPLES

A number of formulations were produced by mixing the constituents outlined in Table 1 by adding the individual constituents into a beaker of deionized water at room temperature which was stirred with a conventional magnetic stirring rod. Stirring continued until the formulation was homogenous in appearance. It is to be noted that the constituents might be added in any order, but it is preferred that a first premixture is made of any fragrance constituent with one or more surfactants used in the inventive compositions. Thereafter, a major amount of water is first provided to a suitable mixing vessel or apparatus as it is the major constituent and thereafter the further constituents are added thereto convenient. The order of addition is not critical, but good results are obtained where the surfactants (which may be also the premixture of the fragrance and surfactants) are added to the water prior to the remaining constituents.

The exact compositions of the example formulations are listed on Table 1, below, and are identified by one or more digits preceded by the letter "E". Certain comparative compositions are also disclosed on Table 1, and are identified by one or more digits preceded by the letter "C".

TABLE 1

| | C1 | E1 | E2 | E3 | E4 | E5 | E6 | E7 |
|---|---|---|---|---|---|---|---|---|
| lactic acid (80%) | 4.0 | 2.5 | 2.5 | 2.5 | 2.5 | 4.0 | 2.5 | 4.0 |
| citric acid | — | 0.12 | 0.12 | 0.12 | 0.12 | 0.12 | 0.12 | 0.12 |
| malic acid | — | 0.12 | 0.12 | 0.12 | 0.12 | 0.12 | 0.12 | 0.12 |
| dipropylene glycol n-butyl ether | 3.0 | 1.0 | 2.0 | — | 2.0 | — | 1.0 | — |
| ethanol (95%) | — | — | — | 2.0 | — | 3.0 | — | 3.0 |
| $C_{10}$ alcohol ethoxylate, 8EO (85%) | — | 1.18 | 1.76 | 0.59 | 1.76 | 0.2 | 1.2 | 0.2 |
| $C_9$-$C_{11}$ alcohol ethoxylate, 6EO (95-100%) | 1.0 | — | — | — | — | — | — | — |
| alkylpolyglucoside (50%) | — | 1.0 | 1.0 | 0.5 | 1.0 | 0.24 | 1.0 | 0.24 |
| sodium $C_{14}$-$C_{17}$ secondary alkyl sulfonate (60%) | 1.0 | 1.67 | 1.67 | 0.42 | 1.67 | 0.3 | 3.33 | 0.6 |
| sodium hydroxide (50%) | 0.54 | 0.38 | 0.38 | 0.54 | 0.38 | 0.38 | 0.38 | 0.54 |
| fragrance (proprietary composition) | 0.25 | — | 0.25 | 0.08 | 0.25 | 0.075 | 0.025 | 0.11 |
| colorant | — | — | — | — | 0.0016 | — | 0.0015 | — |
| deionized water | q.s. | q.s. | q.s. | q.s. | q.s. | q.s. | q.s. | q.s. |
| pH | ≈3 | ≈3 | ≈3 | ≈3 | ≈3 | ≈3 | ≈3 | ≈3 |

All of the formulations on the foregoing Table 1 are indicated in weight percent, and each composition comprised 100% wt. The individual constituents were used, "as-supplied" from their respective source and unless otherwise indicated, each of the constituents are to be understood as being "100% wt. actives". Deionized water was added in quantum sufficient, "q.s.", to provide the balance to 100% wt. of each of the example compositions. The sources of the constituents used in the formulations of Tables 1 are described on the following Table 2.

The example composition, "C1" is based on a presently commercially available hard surface treatment composition.

TABLE 2

| | |
|---|---|
| lactic acid (80%) | lactic acid, 80% wt. active aqueous dispersion/solution |
| citric acid | anhydrous citric acid (100% wt. actives) |
| malic acid | laboratory grade (100% wt. actives) |
| dipropylene glycol n-butyl ether | DOWANOL DPnB (ex. Dow Chem. Co.) (95-100% wt. actives) |
| ethanol (95%) | laboratory grade ethanol (95% wt. actives) |
| $C_{10}$ alcohol ethoxylate, 8EO (85%) | LUTENSOL XP 89 (ex. BASF AG) (85% wt. actives) |
| $C_9$-$C_{11}$ alcohol ethoxylate, 6EO (95-100%) | NEODOL 91-6 (ex. Shell Co.) (95-100% wt. actives) |

TABLE 2-continued

| | |
|---|---|
| alkylpolyglucoside (50%) | GLUCOPON 425N (ex. Cognis, Inc.) (50% wt. actives) |
| sodium $C_{14}$-$C_{17}$ secondary alkyl sulfonate (60%) | HOSTAPUR SAS 60 (ex. Clariant Inc.) (60% wt. actives) |
| sodium hydroxide (50%) | sodium hydroxide, 50% wt. actives aqueous dispersion/solution |
| fragrance (proprietary composition) | fragrance (proprietary composition) |
| colorant | colorant (proprietary composition) |
| deionized water | deionized water |

The foregoing compositions disclosed on Table 1 were used as described in the treatment of hard surfaces.

Two of the formulations of Table 1 were also used to form a wipe type article wherein an absorbent substrate was contacted with at partially impregnated with the compositions according to E5 and E7.

A first exemplary wipe article, identified as example "E5W" was formed by contacting an absorbent substrate in sheet or roll form which absorbent substrate was formed from 40-45% wt. spunbound polypropylene fibers and 55-60% wt. softwood kraft pulp with the formulation according to E5 at a respective weight ratio of formulation E5: absorbent substrate of 4.5:1.

A second exemplary wipe article, identified as example "E7W" was formed by contacting an absorbent substrate in sheet or roll form which absorbent substrate was formed from 50-60% wt. "Viloft" fibers and 40-50% wt. viscose fibers with the formulation according to E7 at a respective weight ratio of formulation E7: absorbent substrate of 3.5:1.

Both the first and second wipe articles formed provided effective hard surface treatment articles.

Several of the foregoing compositions described on Table 1 were tested and evaluated according to one or more of the following test protocols.

Cleaning Evaluation

Cleaning evaluations for greasy soils were performed in accordance with the testing protocol outlined according to ASTM D4488 A2 Test Method, which evaluated the efficacy of the cleaning compositions on masonite wallboard samples painted with wall paint. The soil applied was a greasy soil sample containing vegetable oil, food shortening and animal fat. The sponge (water dampened) of a Gardner Abrasion Tester apparatus was squirted with a 15 gram sample of a tested cleaning composition, and the apparatus was cycled 10 times. The evaluation of cleaning compositions was "paired" with one side of each of the test samples treated with a composition according to the invention, and the other side of the same sample treated with a comparative example's composition, thus allowing a "side-by-side" comparison to be made. Each of these tests were duplicated on at least 4 wallboard tiles and the results statistically analyzed and the averaged results reported on Table 3, below. The cleaning efficacy of the tested compositions were evaluated the cleaning efficacy of the tested compositions was evaluated utilizing a high resolution digital imaging system which evaluated the light reflectance characteristics of the each tested sample wallboard sample. This system utilized a photographic copy stand mounted within a light box housing which provided diffuse, reflected light supplied by two 15 watt, 18 inch type T8 fluorescent bulbs rated to have a color output of 4100K which approximated "natural sunlight" as noted by the manufacturer. The two fluorescent bulbs were positioned parallel to one another and placed parallel and beyond two opposite sides of the test substrate (test tile) and in a common horizontal plane parallel to the upper surface of the test substrate being evaluated, and between the upper surface of the tile and the front element of the lens of a CCD camera. The CCD camera was a "Qlmaging Retiga series" CCD camera, with a Schneider-Kreuznach Cinegon Compact Series lens, f1.9/10 mm, 1 inch format (Schneider-Kreuznach model #21-1001978) which CCD camera was mounted on the copy stand with the lens directed downwardly towards the board of the copy stand on which a test substrate was placed directly beneath the lens. The light box housing enclosed the photographic copy stand, the two 18 inch fluorescent bulbs and a closeable door permitted for the insertion, placement and withdrawal of a test tile which door was closed during exposure of the CCD camera to a test tile. In such a manner, extraneous light and variability of the light source during the evaluation of a series of tested substrates was minimized, also minimizing exposure and reading errors by the CCD camera.

The CCD camera was attached to a desktop computer via a Firewire IEEE 1394 interface and exposure data from the CCD camera was read by a computer program, "Media Cybernetics Image Pro Plus v. 6.0", which was used to evaluate the exposures obtained by the CCD camera, which were subsequently analyzed in accordance with the following. The percentage of the test soil removal from each test substrate (tile) was determined utilizing the following equation:

$$\%\ \text{Removal} = \frac{RC - RS}{RO - RS} \times 100$$

where

RC=Reflectance of tile after cleaning with test product

RO=Reflectance of original soiled tile

RS=Reflectance of soiled tile

The cleaning performance of composition E2 and C1 as identified above on Table 1 were compared, and the averaged results of % Removal of the test soil are reported on the following table.

TABLE 3

| Formulation | % Removal |
|---|---|
| E2 | 81.02 |
| C1 | 77.54 |

As is evident from the foregoing, the compositions exhibited comparable cleaning performance.

Antimicrobial Efficacy

The antimicrobial efficacy of several of the compositions disclosed on Table 1 were evaluated in accordance with the protocols of British Standard EN 13697:2001 for Chemical disinfectants and antiseptics—Quantitative non-porous surface test for the evaluation of bactericidal and/or fungicidal activity of chemical disinfectants used in food, industrial, domestic and institutional areas. According to this test a "pass" score is achieved when there is a 4 $\log_{10}$ reduction of the microorganism at a 5 minute contact time.

TABLE 4

| | $Log_{10}$ reduction | | |
|---|---|---|---|
| | C1 | E1 | E3 |
| *Staphylococcus aureus* | 6.54 | 6.52 | 5.16 |
| *Enterococcus hirae* | 6.72 | 6.71 | 6.38 |
| *Escherichia coli* | 5.79 | 6.26 | 5.33 |
| *Pseudomonas aeruginosa* | 4.71 | 5.81 | 4.78 |

As is readily evident from the results reported on Table 4, the compositions of the invention provided comparable antimicrobial efficacy as compared to the "C1" formulation, but with significantly reduced amounts of lactic acid. All of the tested composition received a "pass" score according to EN 13697 as having achieved in excess of the minimum 4 $\log_{10}$ reduction of the microorganism at a 5 minute contact time.

While the invention is susceptible of various modifications and alternative forms, it is to be understood that specific embodiments thereof have been shown by way of example in the foregoing which are not intended to limit the invention to the particular forms disclosed; on the contrary the intention is to cover all modifications, equivalents and alternatives falling within the scope and spirit of the invention as expressed in the appended claims.

The invention claimed is:

1. An aqueous liquid acidic hard surface treatment composition having a pH of about 3.5 or less which comprises:

0.001-3.5% wt. of an acid constituent which comprises lactic acid, citric acid, and malic acid, wherein the respective weight ratio of the lactic acid:citric acid:malic acid is about 16.6-26.6:1:1;

an organic solvent constituent selected from the group consisting of a $C_1$-$C_6$ monohydric alcohol and/or a glycol ether;

a branched, secondary alkyl sulfate and/or a branched, secondary alkyl sulfonate anionic surfactant;

a nonionic surfactant constituent which comprises a mono-branched alkoxylated C10/C11-fatty alcohol, preferably based on a C-10 Guerbet alcohol, concurrently with at least one alkylpolyglucoside;

optionally a cosurfactant constituent;

optionally one or more further constituents selected from coloring agents, fragrances and fragrance solubilizers, viscosity modifying agents including one or more thickeners, pH adjusting agents and pH buffers including organic and inorganic salts, optical brighteners, opacifying agents, hydrotropes, abrasives, and preservatives;

and the balance, water, wherein water comprises at least 80% wt. of the composition.

2. A composition according to claim 1 wherein: the nonionic surfactant constituent consists solely of a mono-branched alkoxylated C10/C11-fatty alcohol, based on a C-10 Guerbet alcohol, concurrently with an alkylpolyglucoside, to the exclusion of other nonionic surfactants.

3. A composition according to claim 1 wherein the sole anionic surfactant constituent present in the composition is the secondary alkyl sulfonate anionic surfactant.

4. A composition according to claim 1 wherein the organic solvent constituent consists solely of one or more $C_1$-$C_6$ monohydric alcohols and/or glycol ethers, to the exclusion of other organic solvent constituents.

5. A method of cleaning a stained hard surface in need of cleaning which method comprises the step of:

applying a cleaning effective amount of the composition according to claim 1 to a hard surface in need of a cleaning treatment.

6. A method of disinfecting or sanitizing a stained hard surface in need of disinfection or sanitizing which method comprises the step of:

applying a disinfecting or sanitizing effective amount of the acidic hard surface treatment composition according to claim 1 to a hard surface in need of a disinfecting or sanitizing treatment.

7. A composition according to claim 1, wherein the mono-branched alkoxylated C10/C11-fatty alcohol comprises at least 8 mols of ethoxylation.

8. An aqueous liquid acidic hard surface treatment composition having a pH of about 3.5 or less which comprises:

0.001-3.5% wt, of an acid constituent which comprises lactic acid, citric acid, and malic acid, wherein the respective weight ratio of the lactic acid:citric acid:malic acid is about 16.6-26.6:1:1;

an organic solvent constituent selected from the group consisting of a C1-C6 monohydric alcohol and/or a glycol ether;

a sulfur atom containing anionic surfactant;

a nonionic surfactant constituent which comprises at least one ethoxylated nonionic surfactant and at least one alkylpolyglucoside;

optionally a cosurfactant constituent;

optionally one or more further constituents selected from coloring agents, fragrances and fragrance solubilizers, viscosity modifying agents including one or more thickeners, pH adjusting agents and pH buffers including organic and inorganic salts, optical brighteners, opacifying agents, hydrotropes, abrasives, and preservatives;

and the balance, water, wherein water comprises at least 80% wt. of the composition.

* * * * *